(12) United States Patent
Wang et al.

(10) Patent No.: US 10,117,956 B2
(45) Date of Patent: *Nov. 6, 2018

(54) RADIOLABELED ACTIVE TARGETING PHARMACEUTICAL COMPOSITION AND THE USE THEREOF

(71) Applicant: Institute of Nuclear Energy Research Atomic Energy Council, Executive Yuan, Taoyuan County (TW)

(72) Inventors: Hsin-Ell Wang, Taoyuan County (TW); Chien-Chung Hsia, Taoyuan County (TW); Mao-Chi Weng, Taoyuan County (TW); Kun-Liang Lin, Taoyuan County (TW); Hao-Wen Kao, Taoyuan County (TW); Chao-Cheng Chen, Taoyuan County (TW); Kwan-Hwa Chi, Taoyuan County (TW); Der-Chi Tien, Taoyuan County (TW); Wuu-Jyh Lin, Taoyuan County (TW)

(73) Assignee: INSTITUTE OF NUCLEAR ENERGY RESEARCH ATOMIC ENERGY COUNCIL, EXECUTIVE YUAN, Longtan Township (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/704,378

(22) Filed: Sep. 14, 2017

(65) Prior Publication Data
US 2018/0117188 A1    May 3, 2018

Related U.S. Application Data

(62) Division of application No. 14/490,072, filed on Sep. 18, 2014, now Pat. No. 9,789,214.

(30) Foreign Application Priority Data

Sep. 18, 2013 (TW) .............................. 102133825 A

(51) Int. Cl.
*A61K 51/00* (2006.01)
*A61M 36/14* (2006.01)
*A61K 51/10* (2006.01)
*A61K 51/08* (2006.01)
*A61K 51/12* (2006.01)

(52) U.S. Cl.
CPC ........ *A61K 51/1093* (2013.01); *A61K 51/088* (2013.01); *A61K 51/103* (2013.01); *A61K 51/1244* (2013.01)

(58) Field of Classification Search
CPC ............ A61K 2121/00; A61K 2123/00; A61K 51/00; A61K 51/1093; A61K 51/103; A61K 51/08; A61K 51/088; A61K 51/1244
USPC .......... 424/1.11, 1.29, 1.33, 1.37, 1.53, 1.65, 424/1.69, 1.81, 1.85, 1.89, 400, 489; 514/1, 1.1; 530/300; 534/7, 10–16; 977/773
See application file for complete search history.

(56) References Cited

U.S. PATENT DOCUMENTS

| | | | |
|---|---|---|---|
| 8,575,110 B2* | 11/2013 | Burkhard | C07K 14/001 424/184.1 |
| 9,789,214 B2* | 10/2017 | Wang | A61K 51/088 |
| 2011/0044911 A1* | 2/2011 | Akhtari | A61K 41/0052 424/9.34 |
| 2011/0104052 A1 | 5/2011 | Barnett et al. | |

* cited by examiner

*Primary Examiner* — D. L. Jones
(74) *Attorney, Agent, or Firm* — Muncy, Geissler, Olds & Lowe, P.C.

(57) ABSTRACT

The present invention is related to a radiolabeled active targeting pharmaceutical composition, including: a bioconjugate and a radionuclide, wherein the bioconjugate includes a biomolecule and a metal nanoparticle, wherein the biomolecule has an affinity for receptors on the surface of a cell membrane and is selected from the group consisting of a peptide and a protein. The present invention further provides a method for evaluating a thermal adjuvant therapy for tumors and a kit thereof. The above-mentioned pharmaceutical composition is applied to evaluate a tumor accumulation time, so as to establish the optimal policy for a radiofrequency- or laser-induced thermal adjuvant therapy for tumors.

2 Claims, 15 Drawing Sheets

RADIOLABELED ACTIVE TARGETING PHARMACEUTICAL COMPOSITION AND THE USE THEREOF

CROSS-REFERENCE TO RELATED APPLICATIONS

This application is a Divisional of co-pending application Ser. No. 14/490,072 filed on Sep. 18, 2014, for which priority is claimed under 35 U.S.C. § 120; and this application claims priority of application Ser. No. 102133825 filed in Taiwan, R.O.C. on Sep. 18, 2013 under 35 U.S.C. § 119; the entire contents of all of which are hereby incorporated by reference.

BACKGROUND OF THE INVENTION

Field of Invention

The present invention is related to a radiolabeled active targeting pharmaceutical composition and the use thereof, and more particularly, to a pharmaceutical composition of a bioconjugate including a biomolecule (such as a peptide and a protein) and a metal nanoparticle, and the use of the pharmaceutical composition for evaluating a thermal adjuvant therapy for tumors.

Related Art

Cancer is one of the major causes of human deaths. A conventional therapy often removes a tumor through surgery with radiotherapy and chemotherapy combined. In recent years, during the development of cancer treatment drugs, to lower the toxicity on normal tissues, targeted therapy drugs that can be precisely delivered to a treatment region, reduce the delivery times and dosage, and enhance the toxic effect on tumor tissues are under vigorous development. Biomedical materials are being developed; especially, a nanoparticle serves as a drug carrier and the passive targeting characteristic of an enhanced permeation and retention (EPR) effect is adopted to specifically accumulate drugs at a target tumor. In addition, the surface of the drug carrier is modified with a ligand with specificity, such as an antibody, a peptide or an epidermal growth factor (EGF), so that at a focus with high expression of a receptor or an antigen, active targeting increases the accumulation of drugs at a target tumor.

Many malignant tumors have the phenomenon of excessive expression of an epidermal growth factor receptor (EGFR), and the expression of an EGFR of a malignant tumor is closely associated with tumor invasiveness and therapeutic drug resistance. This type of cancer activates the EGFR to facilitate hyperplasia, angiogenesis, and metastasis and lowers apoptosis of the tumor. Therefore, the EGFR has been regarded as an important anticancer drug target in current researches.

Also, Cetuximab (Erbitux®, C225) is a human-mouse hybrid chimeric monoclonal IgG protein and has a high affinity for an EGFR, and is a therapeutic drug for tumors with high expression of an EGFR. An EGF or other ligands contend for combination with the EGFR, so as to prevent phosphorylation of a receptor and activation of relevant ferments of an EGFR to inhibit downstream signal transfer thereof, including hyperplasia, angiogenesis, metastasis, and apoptosis. Pre-clinical test show that cetuximab has obvious efficacy in inhibiting tumor growth both separately and in combination with conventional chemotherapeutic drugs, and was approved by the Food and Drug Administration in 2004, and cetuximab and irinotecan are used in combination to treat patients with metastasic colorectal cancer through expression of an EGFR.

Moreover, macromolecular carriers such as nanoparticles include organic nanoparticles such as liposomes, micelles, and dendrimers and inorganic nanoparticles such as quantum dots, iron oxide nanoparticles, and gold nanoparticles (AuNPs). Vascular endothelial tissues of a tumor have a large gap (up to hundreds of nanometers) to allow the passage of nanoparticles, which permeate from the tumor and accumulate at the tumor; and the lymphatic system of the tumor is underdeveloped, so that drugs cannot return to the circulatory system via the lymphatic system and are retained at the tumor for a long period. Such an effect is the EPR effect above. The EPR effect can be regarded as a passive targeting effect, so that drugs carried by nanoparticles reach desirable dynamic drug distribution. Also, such type of macromolecular carriers cannot penetrate healthy vascular epithelial tissues, resulting in that a very small number of chemotherapeutic drugs carried by nanometers carriers are accumulated at normal tissues. Nanomedicines have found wide application in diagnosis and therapy of cancer.

In inorganic nanoparticles, for example, as AuNPs have distinct localized surface plasma resonance and biocompatibility, various specific ligands such as peptides and proteins can be modified at the surface through the bond of a sulfur group or an amino group; AuNPs are noble metal and have low biological toxicity, so that AuNPs are currently widely used as a medium in hyperthermia therapy of tumors. However, common AuNPs only have a passive targeting effect, and actively targeted AuNPs are the trend and focus of researches in recent years.

In conclusion, so far there is still a need for a pharmaceutical composition with an active targeting capability that has both effective functions of nuclear medicine imaging diagnosis or radionuclide therapy and can effectively evaluate a therapeutic effect.

SUMMARY OF THE INVENTION

In view of the deficiencies in the prior art, an object of the present invention is to provide a radiolabeled active targeting pharmaceutical composition, comprising:

a bioconjugate, comprising: a biomolecule and a metal nanoparticle, where the biomolecule has an affinity for receptors on the surface of a cell membrane and is selected from the group consisting of a peptide and a protein, when the biomolecule is a protein, the biomolecule is further combined with an intercalating agent, and the intercalating agent is 1,4,7,10-Tetraazacyclotetradecane-1,4,7,10-Tetraacetic acid (1,4,7,10-Tetraazacyclotetradecane-1,4,7,10-Tetraacetic acid, DOTA); and a radionuclide, selected from the group consisting of: indium, iodine, lutetium, rhenium, gallium, yttrium, and technetium.

In an implementation aspect, the protein is a monoclonal antibody. For example, in some implementation aspects, a monoclonal antibody is, but not limited to, a chimeric monoclonal IgG antibody. Further, in a specific implementation aspect, the chimeric monoclonal IgG antibody is C225. In another implementation aspect, the protein has an affinity for EGFR.

In an implementation aspect, the peptide has an affinity for gastrin releasing peptide receptor (GRPR). The excessive expression of the gastrin releasing receptor comprises prostate cancer, breast cancer, non-small-cell lung cancer, and the like. In a specific implementation aspect, the peptide is, but not limited to, a Bombesin (BBN) peptide.

In an implementation aspect, the peptide is further combined with an intercalating agent. The intercalating agent is diethylene triamine pentaacetic acid (DTPA).

In an implementation aspect, the above-mentioned intercalating agent that is combined with a protein or peptide is, but not limited to, another different intercalating agent as necessary: ethylenediaminetetraacetic acid (EDTA), nitrilotriacetic acid (NTA), N,N-bis(2-mercaptoethyl)-N,N-diethyl ethylene diamine (BMEDA), deferoxamine, dexrozpxane, and a derivative thereof.

In an implementation aspect, the metal nanoparticle is a noble metal nanoparticle, comprising, but not limited to: Au, Pt, Ir, Pd, Os, Ag, and Fe particles. In a specific implementation aspect, the metal nanoparticle is Au.

In an implementation aspect, the protein further has an acetylthioacetate (ATA) group through surface modification.

In an implementation aspect, the metal nanoparticle further has a thiol group through surface modification.

In an implementation aspect, the peptide is further combined with a lipoic acid derivative. For example, in a specific implementation aspect, the lipoic acid derivative is, but not limited to, maleimido-lipoamide.

In an implementation aspect, the radionuclide is any other radioactive isotope capable of being combined with the bioconjugate as necessary.

Another object of the present invention is to provide a method for evaluating a thermal adjuvant therapy for tumors, comprising:

a. applying the above-mentioned active targeting pharmaceutical composition to a test subject with a tumor;

b. measuring biodistribution data and drug dynamics data of the pharmaceutical composition in the test subject by using single-photon emission computed tomography (SPECT/CT) imaging and biodistribution; and c. evaluating a maximum accumulation time of the pharmaceutical composition at the tumor according to the biodistribution data and drug dynamics data, and deciding a time point for thermal adjuvant therapy for tumors there accordingly.

A further object of the present invention is to provide a kit of evaluating a thermal adjuvant therapy for tumors, comprising:

the above radiolabeled active targeting pharmaceutical composition; and an operation instruction, the operation instruction comprising the following steps:

a. applying the foregoing pharmaceutical composition to a test subject with a tumor;

b. measuring biodistribution data and drug dynamics data of the pharmaceutical composition in the test subject by using SPECT/CT imaging and biodistribution; and c. evaluating a maximum accumulation time of the pharmaceutical composition at the tumor according to the biodistribution data and drug dynamics data, and deciding a time point of a thermal adjuvant therapy for tumors there accordingly.

In an implementation aspect, the tumor comes from a human cancer cell. In a specific implementation aspect, the human cancer cell is, for example, but not limited to, an A549 lung cancer cell strain, a PC-3 prostate cancer cell strain or an MB231 breast cancer cell strain.

BRIEF DESCRIPTION OF THE DRAWINGS

The present invention will become more fully understood from the detailed description given herein below for illustration only, and thus are not limitative of the present invention, and wherein:

FIG. 4 shows changes of cell uptake of $^{111}$In-DOTA-C225-AuNPs in A549 with time (see B);

FIG. 10 shows a MALDI-TOF test result of PEG-lipoamide (compound 5) (see B);

DETAILED DESCRIPTION OF THE INVENTION

Next, the embodiments of the present invention are illustrated in detail with the following examples, but the present invention is not limited thereto. The above and other objects, features, and advantages of the present invention become more comprehensible with the following illustration and accompanying drawings.

I. Preparation and Test Examples of a Radiolabeled Active Targeting Pharmaceutical Composition $^{111}$In-DOTA-C225-AuNPs (I) Preparation Example 1: Preparation of Bioconjugate 1. Synthesis of C225-ATA Please refer to the flow chart of preparation in FIG. 1. Take 4 mg of chimeric monoclonal IgG antibody C255

(0.027 µmol, 2 mg/mL). Add N-succinimidyl-S-acetylthioacetate (SATA, 0.125 mg, 0.54 µmol) to react 1 h at the room temperature. When the reaction is ended, perform purification through a gel filtration method (Sephadex G50 gel filtration column). Use PBS as the elution phase. Collect a tube per milliliter to obtain C225-ATA. Measure the number of tubes containing the C225 antibody with an ultraviolet/visible spectrophotometer (UV/VIS Spectrophotometer). Quantify the concentration of the C225 antibody (C225-SH) and C225-ATA with a protein quantification kit (Bio-Rad Protein Assay).

2. Synthesis of DOTA-C225-ATA

Figure 2:
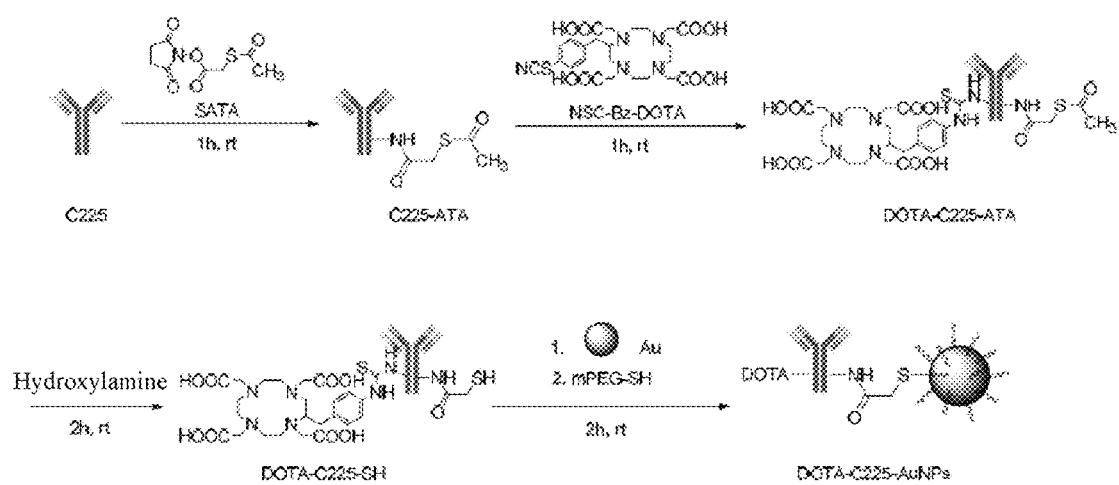
FIG. 2 is a flow chart of preparation of DOTA-C225-AuNPs.

Please refer to the flow chart of preparation in FIG. 2. Take 1 mg of C255 (6.58 nmol). Add (p-benzyl isothiocyanate-1,4,7,10-Tetraazacyclotetradecane-1,4,7,10-Tetraacetic acid (p-SCN-Bz-DOTA, 91.8 µg, nmol) to react 1 h at the room temperature. When the reaction is ended, perform purification through a gel filtration method (Sephadex G50 gel filtration column). Use PBS as the elution phase. Collect a tube per milliliter. Measure the number of tubes containing the C225 antibody with an ultraviolet/visible spectrophotometer (UV/VIS Spectrophotometer). Quantify the concentration of the C225 antibody (C225-SH) and C225-ATA with a protein quantification kit (Bio-Rad Protein Assay).

3. Preparation of Bioconjugate C225-AuNPs and DOTA-C225-AuNPs

Figure 1:
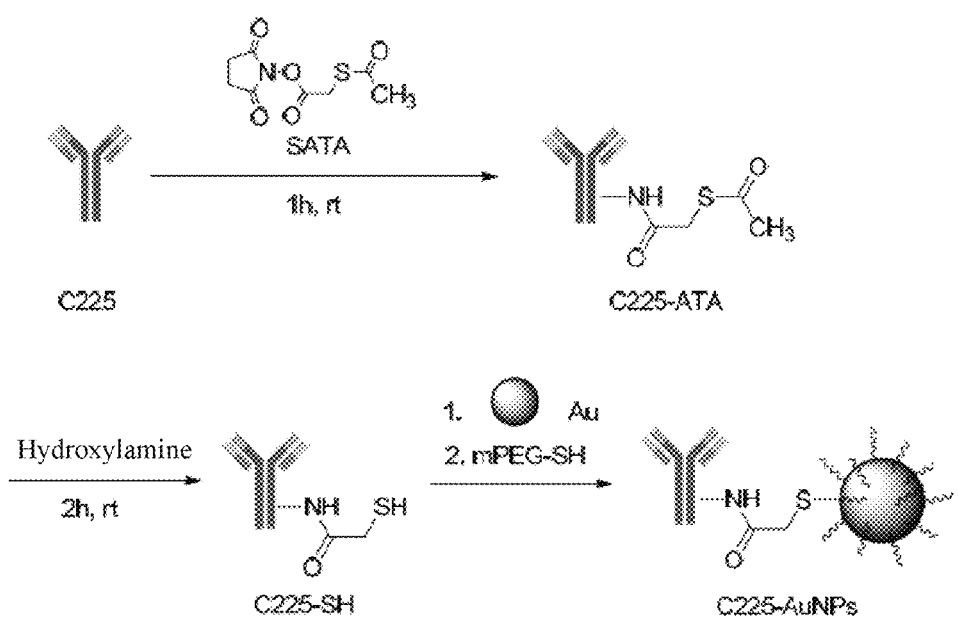
FIG. 1 is a flow chart of preparation of C225-AuNPs.

Please refer to FIG. 1 and FIG. 2, respectively. Take C225-ATA or DOTA-C225-ATA (0.5 mL, 640 µg/mL). Add hydroxylamine (0.5 mL, 50 mM) to react 2 h at the room temperature. Expose —SH and perform purification through a gel filtration method (Sephadex G50 gel filtration column). Add C225-SH or DOTA-C225-SH in an AuNPs solution ($3\times10^{11}$ particles/mL). The protein concentration of the reaction liquid is 50 µg/mL. Perform reaction for 1 h at the room temperature. Add polyethylene glycol-SH (polyethylene glycol-SH, PEG-SH, 0.2 mg/mL) and react another 1 h to completely cover the surface of gold nanoparticles.

Purify C225-AuNPs or DOTA-C225-AuNPs in a centrifugation (3,500 rpm, 10 min×3) manner.

4. Absorption Spectrum of Bioconjugate C225-AuNPs and DOTA-C225-AuNPs

Figure 3:
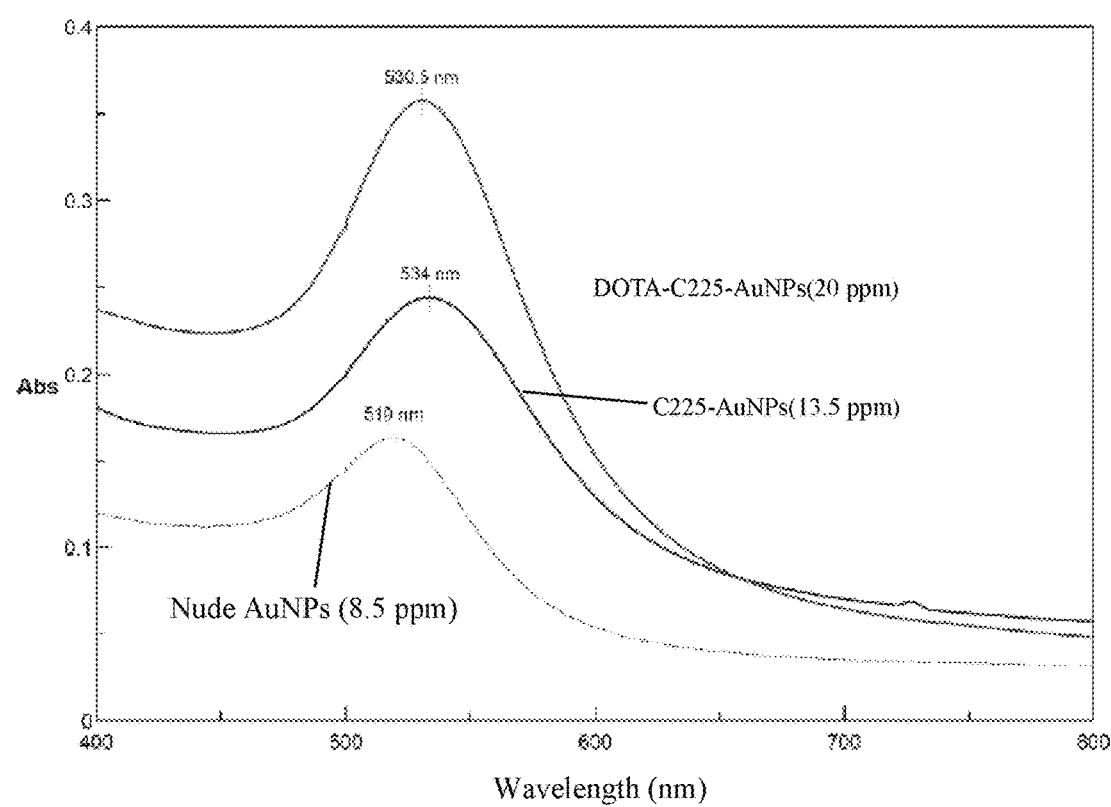
FIG. 3 is an absorption spectrum of bare AuNPs and a bioconjugate (C225-AuNPs and DOTA-C225-AuNPs)

The determination of the characteristics of bioconjugates C225-AuNPs and DOTA-C225-AuNPs, that is, the result of absorption spectrum, is shown in FIG. 3. Compared with bare AuNPs, the maximum absorption wavelength ($\lambda_{max}$) of the bioconjugates C225-AuNPs and DOTA-C225-AuNPs displace from 519 nm to 534 nm and 530.5 nm.

(II) Preparation Example 2: Radioactive Isotope Labelling and Purification for C225 and a Bioconjugate Thereof 1. Iodine-123 Labelling Take 10 µg of C225 (2 mg/mL) or C225-AuNPs. Add an ammonium acetate buffer aqueous solution (0.5 M, pH 5.10) and the demanded radioactive iodine-123 ($Na^{123}I$) solution to the total volume of 100 µL. Perform iodization reaction at the room temperature (25° C.) with Iodogen (50 µg), respectively. When the reaction time (5 minutes) is up, terminate the reaction using 10 µL of $Na_2S_2O_3$ aqueous solution (2 M), and perform radio thin-layer chromatography, in which the stationary phase is RP-18$F_{254S}$, the mobile phase is methanol/buffer aqueous solution=1/1 (v/v). Add 300 µL of PBS to the iodine-123 labelling liquid mixture. Load the Microcon YM-30 thin-membrane filtration kit. Perform centrifugation for 25 minutes (25 min×2) at 4° C. with a high-speed centrifuge (11,000 rpm). When the time is up, invert the filtration membrane. Perform high-speed centrifugation for 10 minutes to obtain the final product $^{123}I$-C225. Perform centrifugation on the $^{123}I$-C225-AuNPs labelling liquid mixture for 10 minutes at 4° C. with a high-speed centrifuge (3,500 rpm) to obtain the final product $^{123}I$-C225-AuNPs.

2. Indium-111 Labelling

Take 10 µg of DOTA-C225 (2 mg/mL) or DOTA-C225-AuNPs. Add a HEPES buffer aqueous solution (0.5 M, pH 6.0) and a demanded radioactive indium-111 ($^{111}InCl_3$) solution in sequence to the total volume of 100 µL. Perform reaction at 37° C. When the reaction time (30 minutes) is up, perform radio thin-layer chromatography, in which the stationary phase is ITLC/SG, and the mobile phase is a citrate buffer (citrate buffer, 0.5 M, pH 6.0) solution. Add 300 µL of PBS to the $^{111}In$-DOTA-C225 labelling liquid mixture and load a Microcon YM-30 thin-membrane filtration kit. Perform centrifugation for 25 minutes (25 min×2) at 4° C. with a high-speed centrifuge (11,000 rpm). When the time is up, invert the filtration membrane. Perform high-speed centrifugation for 10 minutes to obtain the final product $^{111}In$-DOTA-C225. Perform centrifugation on the $^{111}In$-DOTA-C225-AuNPs labelling liquid mixture for 10 minutes at 4° C. with a high-speed centrifuge (3,500 rpm) to obtain the final product $^{111}In$-DOTA-C225-AuNPs.

3. Radioactive Isotope Labelling and Purification Result

The analysis result of the radioactive iodine-123 isotope labelling of C225 shows that the labelling efficiency of iodine-123 for C225 is about 85%. Load the reaction liquid mixture in a Microcon YM-30 thin-membrane centrifugation filter cartridge to remove unreacted iodine-123 ions through centrifugal filtration to obtain the purified $^{123}I$-C225 product. The radio thin-layer chromatography result shows that the purified product has a radiochemical purity >98%, and a radiochemical yield >70%.

The DOTA-C225 result of radioactive indium-111 isotope labelling is similar to iodine-123. The purified product $^{111}In$-DOTA-C225 has a radiochemical purity >98%, and a radiochemical yield >70%.

For radioactive iodine-123 and indium-111 isotope labelling of the bioconjugates (C225-AuNPs and DOTA-C225-AuNPs), the analysis result shows that the labelling efficiencies are about 50% and 55%, respectively, and through centrifugal purification, the purity of the product radiochemical is higher than 95%.

(III) Test Example 1: In Vitro Test

1. Cell Culture

The entire cell culture is processed in a sterile laminar flow cabinet. A lung cancer cell strain A549 (human lung carcinoma) is cultured in a constant-temperature chemostat of 37° C. and 5% $CO_2$ with a Ham's F12K medium containing 10% of fetal bovine serum (FBS).

2. Cell Uptake Test

Grow $2\times10^5$ A549 tumor cells in a 6-well culture plate. When the cells occupy about 60-70% of the culture plate, perform the cell test. Before the test, place the culture medium at a 37° C. water bath till a balance. Take and add $^{111}In$-DOTA-C225-AuNPs with the concentration being about 1 µCi/mL. After even mixing, replace the original culture media in the culture plate with a culture media containing a radioactive tracer. After placement in the 37° C. constant-temperature cell chemostat for 1, 2, 4, and 16 h. Take out the culture plate (n=5) at each time point. Remove the cell culture media. Clean the cells with a PBS solution of 4° C. Take the cells from the culture plate by using a trypsin. Measure the cell radioactivity with a γ-counter.

3. Test Result

Figure 4:
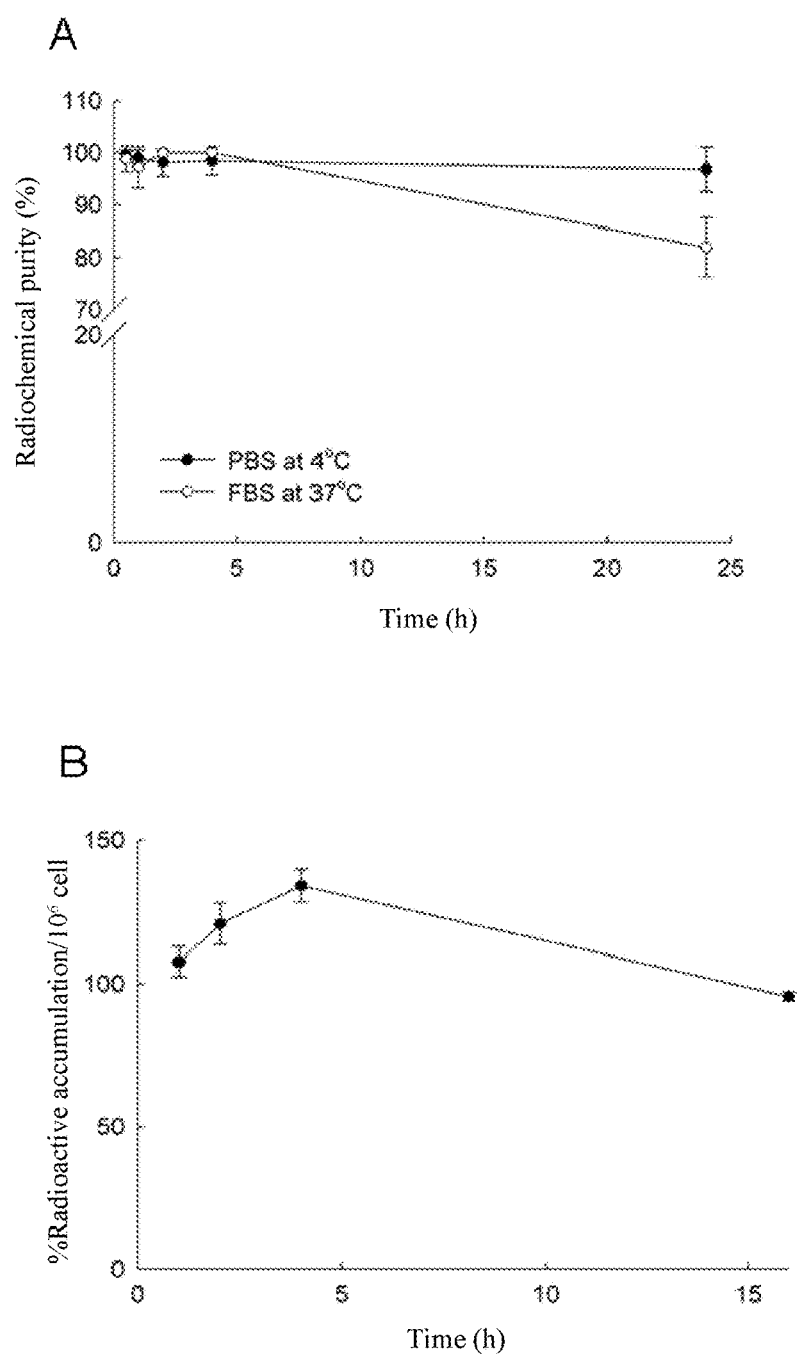
FIG. 4 shows the radiochemical stability of $^{111}$In-DOTA-C225-AuNPs in phosphate-buffered saline (PBS) (4° C.) and in fetal bovine serum (37° C.) measured at different time (see A)

Please refer to FIG. 4. FIG. 4 (panel A) shows the radiochemical stability of $^{111}$In-DOTA-C225-AuNPs in PBS (4° C.) and fetal bovine serum (37° C.) measured at different time. FIG. 4 (panel B) shows changes of cell uptake of $^{111}$In-DOTA-C225-AuNPs in A549 with time. The test result shows that $^{111}$In-DOTA-C225-AuNPs has desirable stability in the PBS (4° C.). After 24 hours, the radiochemical purity is still >95%. The stability of $^{111}$In-DOTA-C225-AuNPs is acceptable in the serum (fetal bovine serum), and the radiochemical purity is still >80% after 24 hours (FIG. 4, panel A). The uptake of $^{111}$In-DOTA-C225-AuNPs by the A549 lung cancer cell with high expression of EGFR increases with time, and reaches the maximum 133.9±5.7% AD/10$^6$ cell at 4 h (FIG. 4, panel B).

(IV) Test Example 2: In Vivo Test

1. Tumor Induction

First, complete the preparation of instruments required by the test, tumor cells (A549 adenocarcinomic human alveolar basal epithelial cells), and anesthetics for anesthetizing animals, and ensure the sterilization of the instruments. After anesthetizing a nude mouse, extract a tumor cell suspension with a syringe to perform hypodermic injection. After a proper period of time, the tumor is successfully induced.

2. SPECT/CT

After anesthetizing a tumor-carrying mouse, inject 11.1 MBq (300 μCi in 100 μL) of $^{111}$In-DOTA-C225-AuNPs, $^{111}$In-DOTA-C225, $^{123}$I-C225-AuNPs or $^{123}$I-C225 through a tail vein, respectively. Perform generalized radioactive medicine distribution scanning on the test animal by using high resolution SPECT/CT imaging at 2 and 4 hours after injection.

3. SPECT/CT Test Result

Figure 5:
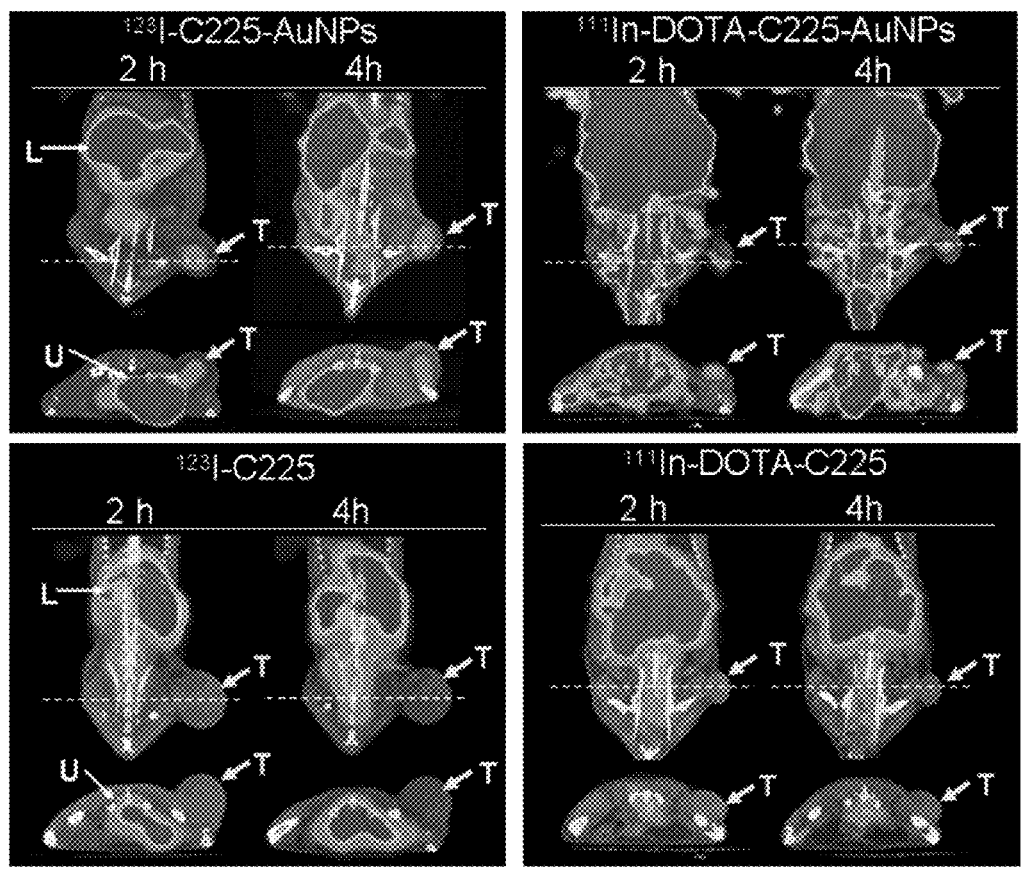
FIG. 5 shows SPECT/CT images and tumor-to-muscle (T/M) ratios thereof 2 and 4 hours after injecting $^{123}$I-C225-AuNPs, $^{123}$I-C225, $^{111}$In-DOTA-C225-AuNPs and $^{111}$In-DOTA-C225 to a mouse carrying A549 tumor, in which L represents liver, T represents tumor, U represents urinary bladder, and in the image of each time point, the upper is a coronal view, and the lower is a transaxial view.

Please refer to FIG. 5. FIG. 5 shows a test result of SPECT/CT imaging at 2 and 4 hours after $^{111}$In-DOTA-C225-AuNPs and $^{123}$I-C225-AuNPs (~300 μCi) are injected into a Balb/c nude mouse hypodermically carrying A549 tumor through a tail vein, respectively. It can be seen from the image that the A549 tumor of the mouse has distinct radioactive accumulation, and has a high T/M ratio (please refer to Table 1). At 4 hours after injection, the T/M ratios reach 5.8 and 6.7, respectively. As nanoparticles are engulfed through a reticuloendothelial system (for example, a liver and a spleen) and is then eliminated by the circulatory system, distinct radioactive accumulation appears in the abdominal cavity of the mouse. In addition, it is also observed in the image that a high radioactive accumulation appears at the urinary bladder portion. Compared with the bioconjugates (C225-AuNPs and DOTA-C225-AuNPs), for radiolabeled C225 that is not combined with the AuNPs, both $^{123}$I-C225 and $^{111}$In-DOTA-C225 have very low radioactivity of tumor accumulation at 2 and 4 hours after injection, and the T/M ratio is about 1. The imaging result shows that the AuNPs combined with radiolabeled C225 are rapidly took up by the tumor with excessive expression of EGFR in vivo, is metabolized by an organ rich in reticuloendothelial systems, and is finally discharged from the body through the urinary system.

TABLE 1

Tumor-to-muscle ratio of labeled antibody C225 and bioconjugate

|  | 2 hours | 4 hours |
|---|---|---|
| $^{123}$I-C225-AuNPs | 4.79 | 6.669 |
| $^{123}$I-C225 | 0.96 | 0.67 |
| $^{111}$In-DOTA-C225-AuNPs | 8.35 | 5.80 |
| $^{111}$In-DOTA-C225 | 1.20 | 1.20 |

4. Biodistribution and Drug Dynamics Test

Perform biodistribution test on mice carrying A549 tumor, which are placed in 5 groups, 4 mice per group. Inject 3.7 MBq (100 μCi in 100 μL) of $^{111}$In-DOTA-C225-AuNPs to each mouse through the tail vein, respectively. Sacrifice one group of mice 0.5, 1, 2, 4, and 24 hour after injection. Pick organ samples rapidly, including organs such as blood, lung, heart, liver, small intestine, large intestine, kidney, spleen, urinary bladder, urine, and muscle and tumor. Weigh them and measure the radioactivity thereof by using a γ-counter, and perform conversion into % ID/g (% injection dose per gram of organ). Analyze the distribution of the radioactive drug in each organ at each time point. The distribution curve of drug concentration at different time points obtained from blood is analyzed by using drug dynamics analysis software WinNonlin, so as to calculate the half life of the drug in the blood.

4. Biodistribution Test Result

By injecting an iodine-131 labeled bioconjugate ($^{131}$I-C225-AuNPs) in a mouse hypodermically carrying A549 lung cancer tumor through a tail vein, perform a biodistribution test at 0.5, 1, 2, 4 and 24 hours after injection, and the results are shown in Table 2. At 30 minutes after injection, the radioactivity in the blood is 3.76±0.98 and later gradually lowers with time. It is shown that the iodine-131 labeled bioconjugates are massively took up and metabolized by organs rich in reticuloendothelial systems (liver, spleen, medulla, and the like) within a short time (30 minutes) after injection, and a certain degree of deiodination occurs, causing distinct radioactive accumulation at the stomach, and free iodine-131 ions are rapidly discharged into the urine, which is consistent with the SPECT/CT observation result.

TABLE 2

Biodistribution test result (n = 4) of mice carrying A549 tumor at 0.5, 1, 2, 4, and 24 hours after injecting of $^{131}$I-C225-AuNPs through a tail vein. Data shown in table with % ID/g.

| Time (h) | 0.5 | 1 | 2 | 4 | 24 |
|---|---|---|---|---|---|
| Blood | 3.76 ± 0.98 | 3.49 ± 0.15 | 3.31 ± 1.08 | 2.84 ± 0.45 | 0.15 ± 0.01 |
| Heart | 0.91 ± 0.12 | 1.13 ± 0.17 | 0.99 ± 0.32 | 1.03 ± 0.26 | 0.05 ± 0.00 |
| Lung | 4.87 ± 2.52 | 6.66 ± 3.72 | 3.85 ± 3.95 | 3.87 ± 1.15 | 0.73 ± 0.25 |
| Liver | 19.47 ± 1.47 | 17.31 ± 1.39 | 18.64 ± 1.82 | 14.15 ± 1.19 | 4.84 ± 0.57 |
| Stomach | 5.80 ± 1.00 | 9.14 ± 0.84 | 11.24 ± 4.28 | 10.86 ± 2.90 | 0.16 ± 0.02 |
| Small intestine | 1.67 ± 0.23 | 1.63 ± 0.29 | 1.89 ± 0.67 | 2.24 ± 0.73 | 0.09 ± 0.04 |

TABLE 2-continued

Biodistribution test result (n = 4) of mice carrying A549 tumor at 0.5, 1, 2, 4, and 24 hours after injecting of $^{131}$I-C225-AuNPs through a tail vein. Data shown in table with % ID/g.

| Time (h) | 0.5 | 1 | 2 | 4 | 24 |
|---|---|---|---|---|---|
| Large intestine | 1.15 ± 0.42 | 1.13 ± 0.21 | 1.02 ± 0.47 | 1.38 ± 0.20 | 0.07 ± 0.02 |
| Spleen | 16.41 ± 3.90 | 17.75 ± 7.71 | 17.91 ± 3.18 | 18.65 ± 3.93 | 6.09 ± 0.34 |
| Kidney | 3.80 ± 0.65 | 3.42 ± 0.43 | 3.08 ± 0.41 | 2.47 ± 1.19 | 0.91 ± 0.07 |
| Muscle | 0.57 ± 0.16 | 0.64 ± 0.05 | 0.58 ± 0.33 | 0.65 ± 0.15 | 0.02 ± 0.01 |
| Urine | 286.9 ± 75.38 | 309.9 ± 2.61 | 169.4 ± 22.38 | 75.08 ± 23.02 | 4.43 ± 1.31 |
| Medulla | 6.58 ± 2.22 | 5.64 ± 2.37 | 3.60 ± 1.37 | 3.86 ± 0.86 | 1.70 ± 0.64 |
| Tumor | 1.75 ± 0.49 | 1.69 ± 0.20 | 1.46 ± 0.71 | 1.66 ± 0.42 | 0.11 ± 0.02 |

Expressed by % injection dose per gram of organ expression (% ID/g), and each value represents an average value ± SD (n = 4)

5. Drug Dynamics Test Result

The in vivo half life of $^{131}$I-C225-AuNPs is calculated via WinNonlin 6.3 (Pharsight®) (by adopting a non-compartment model) to obtain a drug dynamics parameter AUC (area under curve, the area under the time and drug concentration curve), $T_{1/2}$ (the physiological half life in blood) and Cl (clearance rate, the clearance rate of the drug by the blood) shown in Table 3. For the bioconjugate in the present application, when C225 is combined with the AuNPs, the physiological half life significantly reduces from 79-129 h to 5 h. In previous research, Roa et al. reported that after injecting AuNPs (particle diameter being about 20 nm) combined with 6-fluoro-6-deoxy-D-glucose (6-FDG) in a tumor-carrying mouse, after 5 minutes, the concentration in the blood is only 0.59% ID/g, which is much lower than that when 6-FDG is directly injected (30 minutes after injection, the concentration in the blood is still 1.11% ID/g), showing that the AuNPs are the major factors of regulating drug dynamics.

TABLE 3

Drug dynamics parameter calculated from activity-time curve

| Parameter | Unit | Value |
|---|---|---|
| T½ | h | 4.97 |
| Cmax | % ID/mL | 3.76 |
| Cl | μCi/h × (% ID/mL) | 1.13 |
| AUClast | h × % ID/mL | 43.25 |
| AUCinf | h × % ID/mL | 44.34 |

It is proved through the fore-going preparation example provided by the present application that a bioconjugate containing an antibody and a metal nanoparticle is successfully prepared, and a radioactive iodine-123 and indium-111 labeled and purified pharmaceutical composition with an active targeting capability is further prepared. The distribution and drug dynamics of the pharmaceutical composition in the tumor-carrying animal are measured through the test example by using SPECT/CT imaging and biodistribution, so as to evaluate the maximum accumulation time thereof in the tumor after the combination with a radioactive isotope. Based on the result of the test example, it is found that the optimal time of performing other induced thermal adjuvant therapy for tumors such as radiofrequency, infrared, magnetic heating or laser is 4 hours after the above pharmaceutical composition is applied.

II. Preparation and Test Examples of Radiolabeled Active Targeting Pharmaceutical Composition $^{111}$In-BBN-PEG-DTPA-AuNP ($^{111}$In-BPDA)

(I) Preparation Example 1: Preparation of a Bioconjugate BBN-PEG-DTPA-AuNP (BPDA)

1. Compound 1: Synthesis of CBBN

Figure 6:
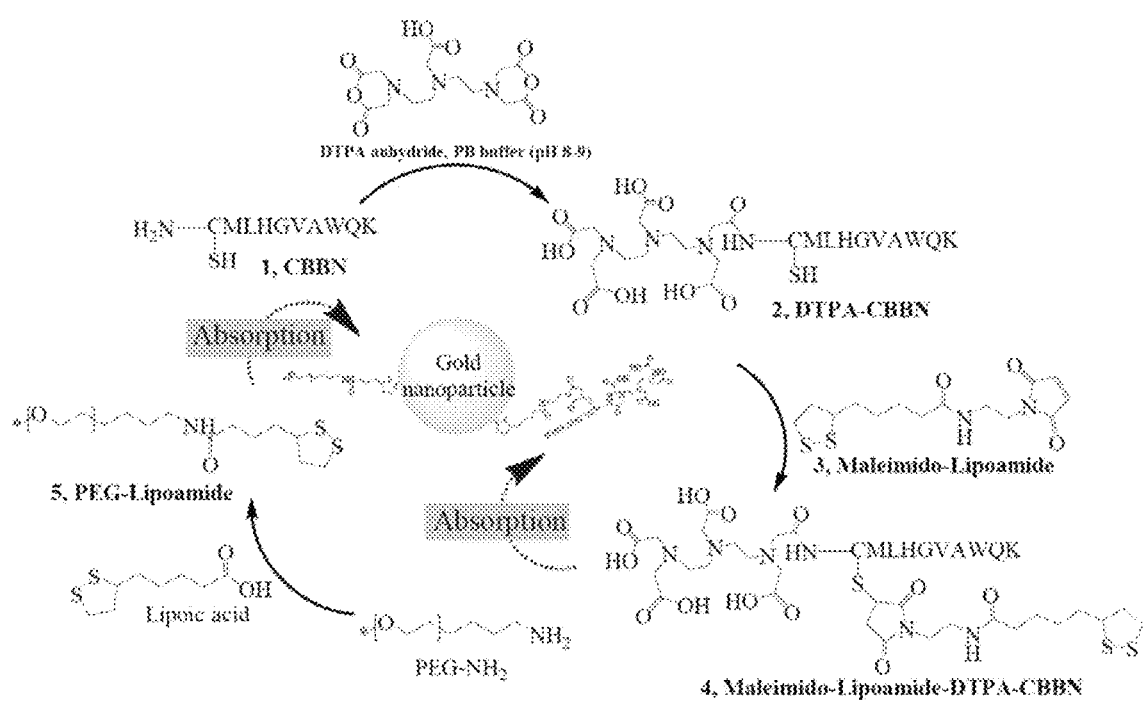
FIG. 6 shows a schematic view of synthesis of a bioconjugate BBN-PEG-DTPA-AuNP (BPDA)

Please refer to FIG. 6. FIG. 6 is a schematic view of synthesis of a bioconjugate BBN-PEG-DTPA-AuNP (BPDA).

The synthesis applies a microwave synthesizer of a peptide synthesizer Liberty 1 (CEM, Liberty 1, USA) to automatically synthesize a demanded sequence. Prepare 0.2 M solution of amino acid in Dimethylformamide (DMF). Prepare coupling reagents HBTU and HOBt (0.5 M, DMF) and a catalyst DIEA (2 M, NMP) in a reaction flask. Further prepare 20% piperidine for removing the amino protecting group. Complete reagent injection and reaction with a Liberty 1 automatic sampling system. The reaction takes 9 hours to complete synthesis. First, in step 1, remove the amino protecting group (Fmoc) using piperidine. Next, in step 2, perform condensation using the HBTU and HOBt. Repeat the two steps. Clean the resin using methanol when the synthesis is ended. Perform hydrolysis on the resin using a TFA/phenol/TES/water/EDT (82.5:5:5:5:2.5) solution. Stir for about three hours. Perform precipitation using ether. Further clean twice using ether. Perform centrifugation, decompression, and drying to obtain a white solid product. This white solid product still has impurities. Further perform separation (MeOH/DDH$_2$O: 1/10-4/1) using a flow injection analysis and collection system (medium performance liquid chromatograph, MPLC) (Teledyne Isco, Combiflash Rf, USA) to finally decompress and concentrate the purified liquid, add water, and freeze to obtain a white solid product, the yield being about 60%. The synthesis sequence this time is CQWAVGHLM. The calculated value of the MS (ESI) of $C_{46}H_{70}N_{14}O_{10}S_2$ [M+H]$^+$ is: 1043.27, and the test value is: 1045.39.

2. Compound 2: Synthesis of DTPA-CBBN

First, take compound 1 (70 mg, 0.067 mmol). Place it in a round-bottom flask and add 0.5 milliliter of a phosphoric acid buffer (pH 8). After CBBN dissolves, add DTPA dianhydride (239.6 mg, 0.67 mmol). Observe changes of the molecular mass of CBBN in the reaction process. The reaction is completed when it is observed with a mass spectrometer (LTQ-MS, Thermo, LTQ-XL Orbitrap, USA) that the molecular mass of CBBN disappears. Next, add 1 M of HCl to dissolve the product. As the product reacts in an alkaline environment to precipitate, subsequently, the product is separated using MPLC. The collection liquid is decompressed, concentrated, and frozen, so as to obtain 28.5 milligrams of a white solid compound 2, the yield being 30%. The calculated value of the MS (ESI) of $C_{60}H_{91}N_{17}O_{19}S_2$ [M+H]$^+$ is: 1418.61, and the test value is: 1420.67.

3. Compound 3: Synthesis of Maleimido-Lipoamide

After the reaction of DTPA-CBBN is completed, the process that (2-Aminoethyl)-maleimide further reacts with the lipoic acid reduces the yield and makes it impossible to separate the byproduct. Therefore, in this embodiment, maleimido-lipoamide is synthesized first. Take (2-Aminoethyl)-maleimide (0.3 g, 1.1 mmol) and lipoic acid (0.2 g, 0.9 mmol) and dissolve them in 3 mL of DMF. Add HOBt (0.17 g, 1.1 mmol), HBTU (0.4 g, 1.0 mmol), and DIEA (0.2 mg, 1.5 mmol) in the reaction flask. React for 8 hours. Observe the reaction using the LTQ-MS. When the reaction is ended, add water of a volume five times as large, and extract twice using 5 mL of DCM. Collect an organic layer. Subsequently, further extract the organic layer using 20 mL of 0.5N HCl twice. Take the organic layer. Finally, perform extraction using 10 mL of saturated NaCl solution once. Add anhydrous magnesium sulfate to the organic layer and perform decompression and drying, so as to obtain 191.3 milligrams of a yellowish solid product 3, the yield being 60%.

Figure 7:
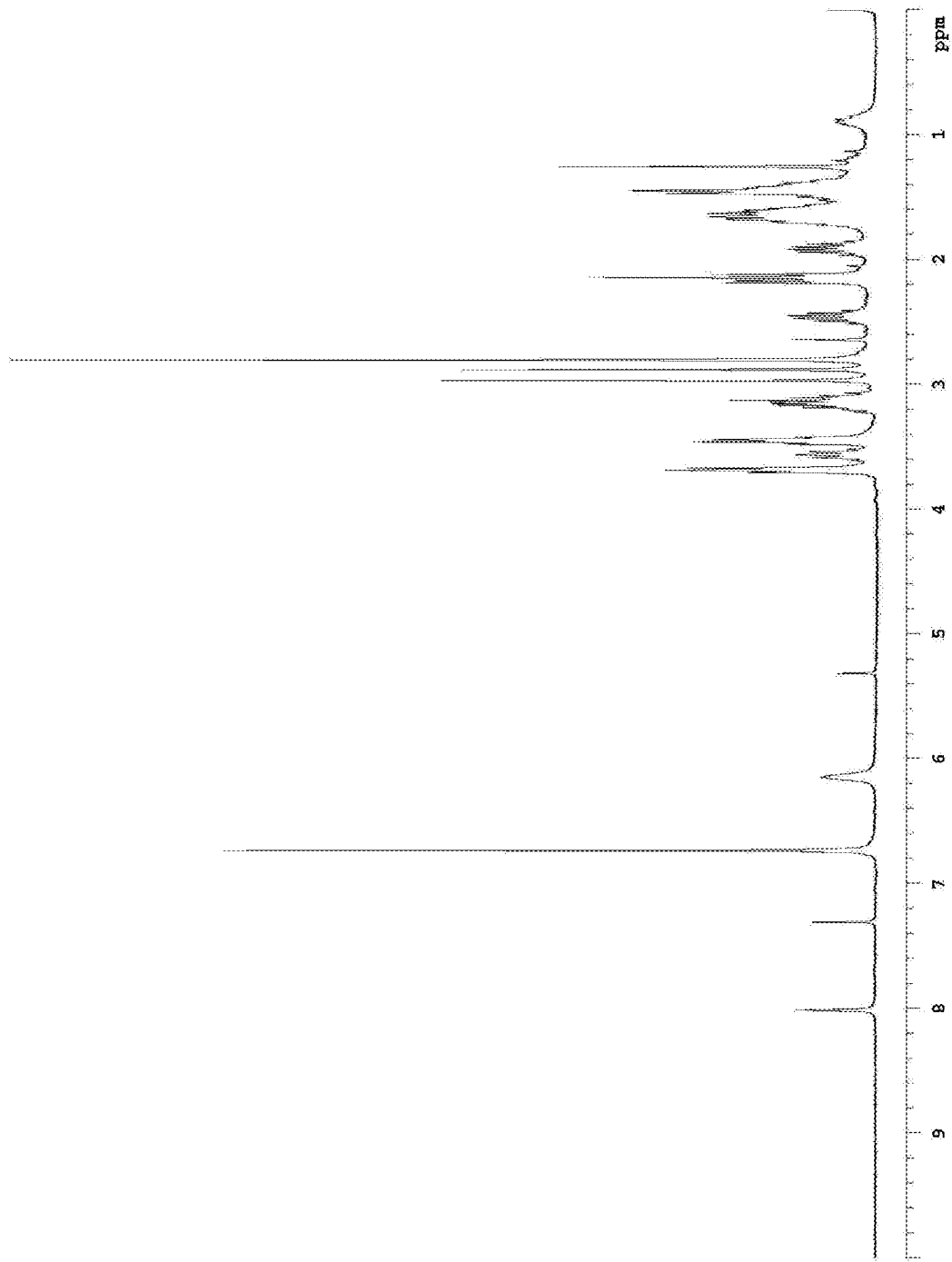
FIG. 7 shows a nuclear magnetic resonance (NMR) result of a lipoic acid.
Figure 8:
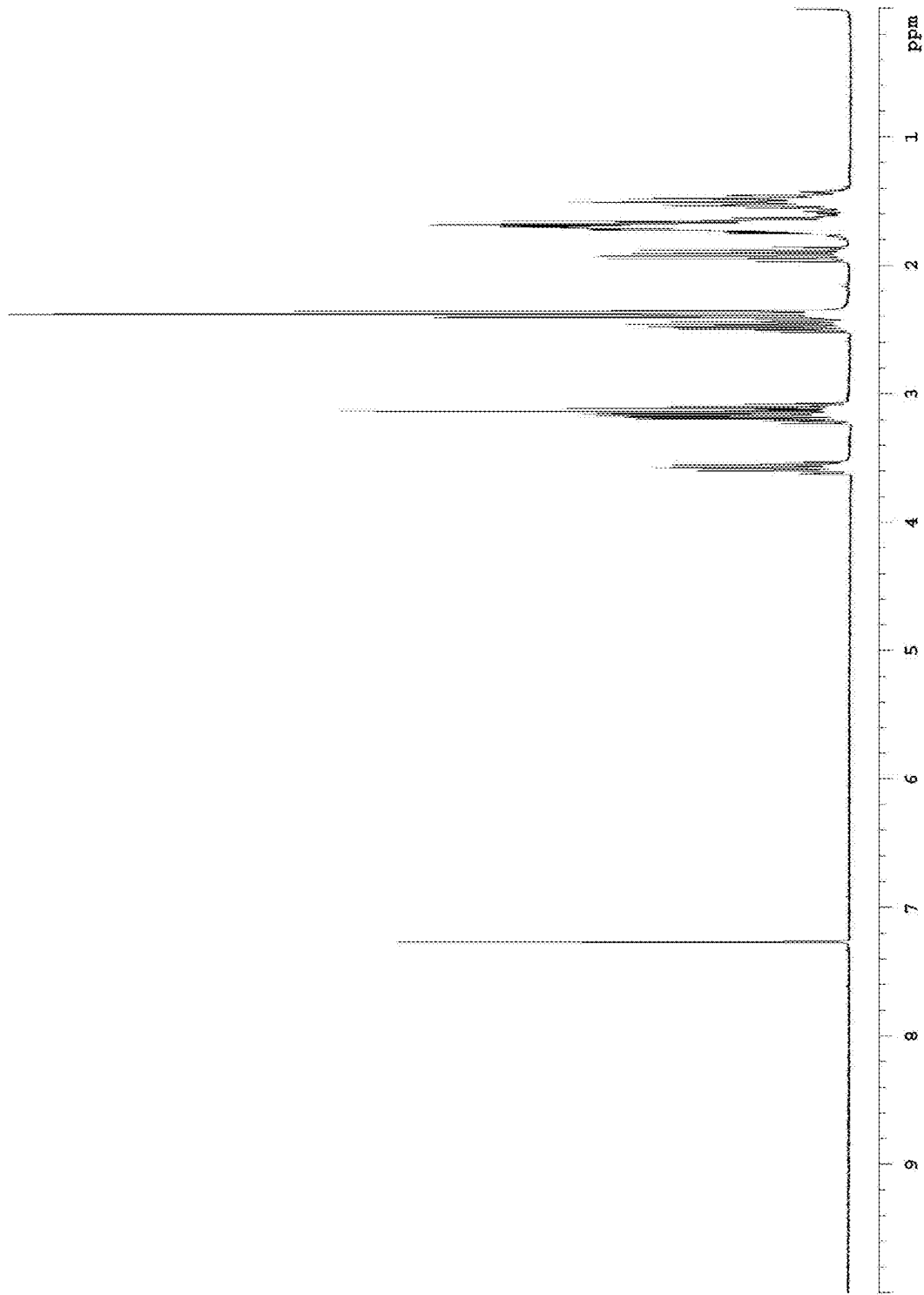
FIG. 8 shows an NMR result of maleimido-lipoamide (compound 3)

The final product result is also verified using NMR, and the results are shown in FIG. 7 and FIG. 8. FIG. 7 is an NMR result of the lipoic acid, and FIG. 8 is an NMR result of compound 3. The calculated value of the MS (ESI) of $C_{13}H_{18}N_2O_3S_2[M+H]^+$ is: 314.42, and the test value is: 361.0$[M+2Na]^{2+}$.

The NMR result is: 1H (CDCl$_3$, 300 MHz) δ=1.447 (m, 3H), 1.631 (m, 3H), 1.92 (m, 1H), 2.12 (dd, 2H), 2.45 (m, 1H), 3.13 (m, 2H), 3.46 (q, 2H), 3.56 (m, 1H), 3.69 (t, 2H), and 6.73 (s, 2H).

4. Compound 4: Synthesis of Maleimido-Lipoamide-DTPA-CBBN (Maleimido-Lipoamide)

Figure 9:
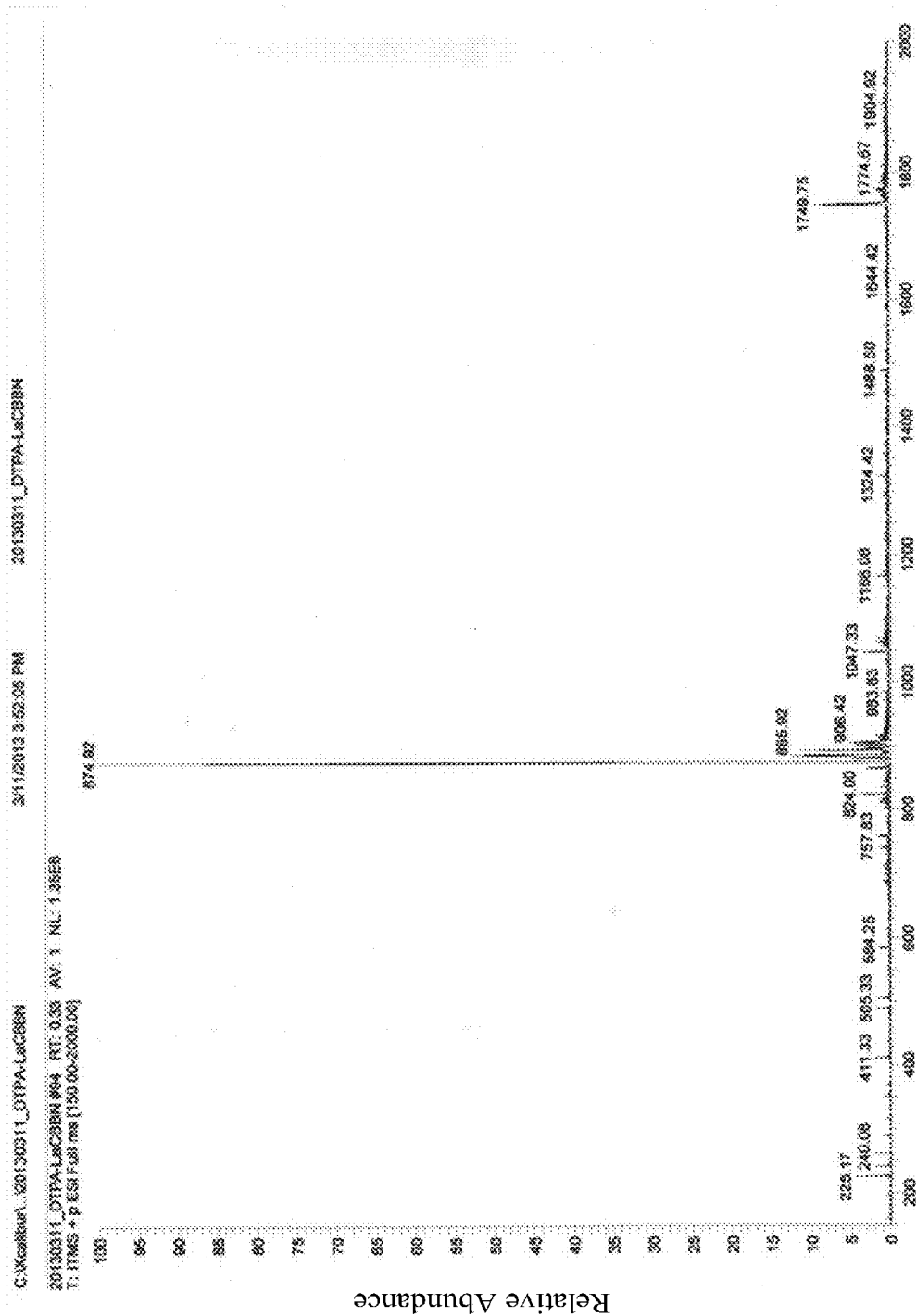
FIG. 9 shows a linear trap quadrupole-mass spectrometry (LTQ-MS) result of maleimido-lipoamide-DTPA-CBBN (compound 4)

Take DTPA-CBBN (10 mg, 0.014 mmol) and maleimido-lipoamide (2.7 mg, 0.016 mmol) to react 8 hours in 1 ml of phosphoric acid buffer (pH 7.0). The reaction endpoint is determined by whether a DTPA-CBBN signal disappears through observing the reaction using the LTQ-MS. When the reaction is ended, directly separate with MPLC, and perform decompression, drying, and then freezing on the collection liquid to obtain 1.7 mg of yellowish solid compound 4, the yield being 14%. The calculated value of the MS (ESI) of $C_{73}H_{109}N_{19}O_{22}S_4 [M+H]^+$ is: 1747.06, and the test value is: 1749.75. The LTQ-MS result of the compound is shown in FIG. 9. The results of mass peaks $[M+H]^+$ and $[M+2H]^{2+}$ of the compound can be seen.

5. Compound 5: Synthesis of PEG-Lipoamide

Take PEG-NH$_2$ (50 mg, 0.02 mmol) and a lipoic acid (4.12 mg, 0.02 mmol) and dissolve them in 3 ml of DMF. Take HOBt (4.6 mg, 0.03 mmol), HBTU (11.4 mg, 0.03 mmol), and DIEA (7.7 mg, 0.06 mmol) and add them in a reaction flask. Stir overnight. Add 10 mL of ether to enable the product to precipitate. After centrifugation, clean the product twice using ether. Perform centrifugation again to collect the precipitate. Separate the product using MPLC. Decompress, concentrate, and freeze the collection liquid to obtain 90 milligrams of yellowish compound 5, the yield being 60%. MALDI-TOF m/z (SA) $[M+H]^+$: it is measured that the molecular mass of compound 5 is about 2412.791.

Figure 10:
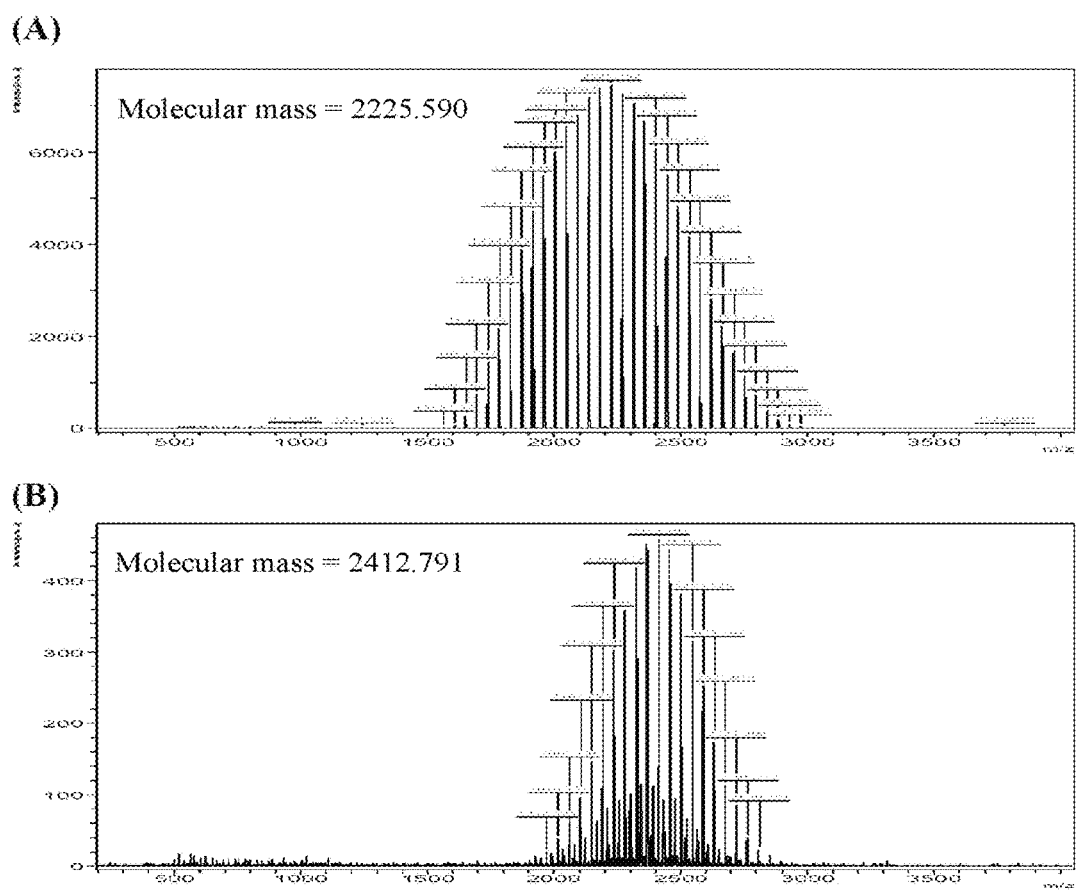
FIG. 10 shows a matrix-assisted laser desorption/ionization time-of-flight (MALDI-TOF) result of a precusor PEG-NH$_2$ (see A)

As shown by the MALDI-TOF test result in FIG. 10, the result of subtracting the molecular mass (2225.590) of the precusor PEG-NH$_2$ is 2412.791−2225.590=187.201, which is quite consistent with the molecular mass (206.33) of the lipoic acid.

6. Bioconjugate: Synthesis of BBN-PEG-DTPA-AuNP (BPDA)

Add maleimido-lipoamide-DTPA-CBBN (0.2 mg, 11 nmol) of compound 4 and PEG-lipoamide (0.2 mg, 83 nmol) of compound 5 in an AuNP solution (volume being 1 mL). The weight ratio of reaction is 1:10. The test tube eppendorf for reaction is sealed with a seal film parafilm and is placed in a dark place at the room temperature. Keep stirring to react 2 hours. When the reaction is ended, perform purification in a centrifugation manner.

Perform centrifugation (12,000 rpm) on the test tube eppendorf. When the centrifugation is finished, suck the supernate. Further add 700 μL of water. Repeat the step three times in total, which is mainly to separate maleimido-lipoamide-DTPA-CBBN of compound 4 and PEG-lipoamide of compound 5 that are not adsorbed on the AuNPs. Finally, store the product BPDA in a dark, 4° C. refrigerator, and measure the particle diameter applying a dynamic light scatter and measure a zeta potential.

Figure 11:
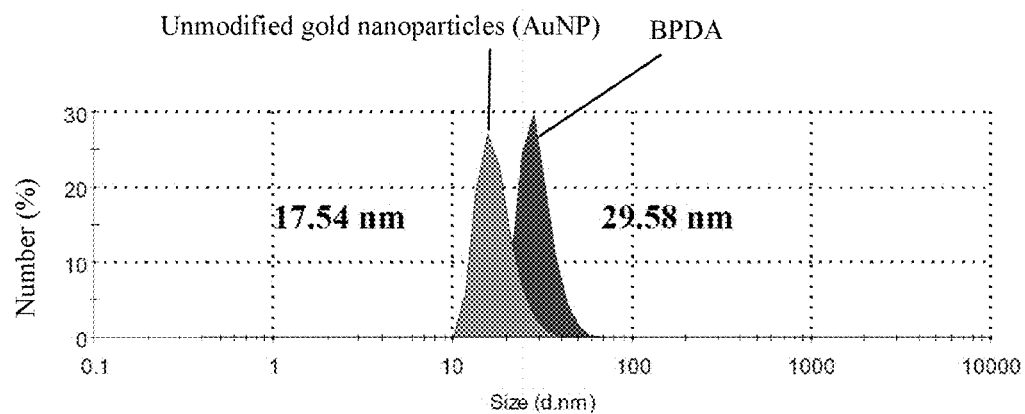
FIG. 11 shows a test result of measuring the particle diameter of BPDA with a dynamic light scatter.

(II) Test Example of BPDA: Measure Characteristics of BPDA Using Dynamic Light Scatter 1. Particle Diameter The principle of dynamic light scattering (DLS, Nano-ZS, Malvern instrument, United Kingdom) is to irradiate the surface of suspended particles scattered in a phase with a single-wavelength laser, measure the attenuation condition of the intensity of reflected light at several angles of reflection or the intensity of reflect light at one fixed angle, and further obtain the average sizes and distribution of the particles on the basis of the light absorption coefficient of the solution and the refraction index of the surface material in combination with a theoretical analysis mode. Prepare the aqueous solution sample containing the test subject BPDA and the gold nanoparticles AuNPs into 1 mL of aqueous solution, respectively, which are filled in a color comparison tube. By applying the function of the Nano-zetasizer of the dynamic light scatter, measure the hydration diameter of the particles, so as to discuss the stability of nanoparticles. As shown in FIG. 11, the results of the test subject BPDA and the gold nanoparticles AuNP in this time of measurement are 29.58 nm and 17.54 nm, respectively, and it can be found that large particle diameters are achieved through modification of BPDA.

2. Zeta Potential

A zeta potential refers to a static voltage induced by ions accumulated on colloid particles in colloidal chemistry. A colloid particle is formed of double-layer electrons, which comprises a fixed layer and a diffusion layer. The electrophoretic mobility of one particle can be obtained through the Henry's function, so as to further calculate the value of the zeta potential thereof. The test of zeta potential requires measurement in the form of an aqueous solution. The ionic aqueous solution affects the practical surface charge of the magnetic nanoparticle in the aqueous solution, and accurate measurement is possible only when the particle concentration is greater than or equal to 1 mg/mL.

Figure 12:
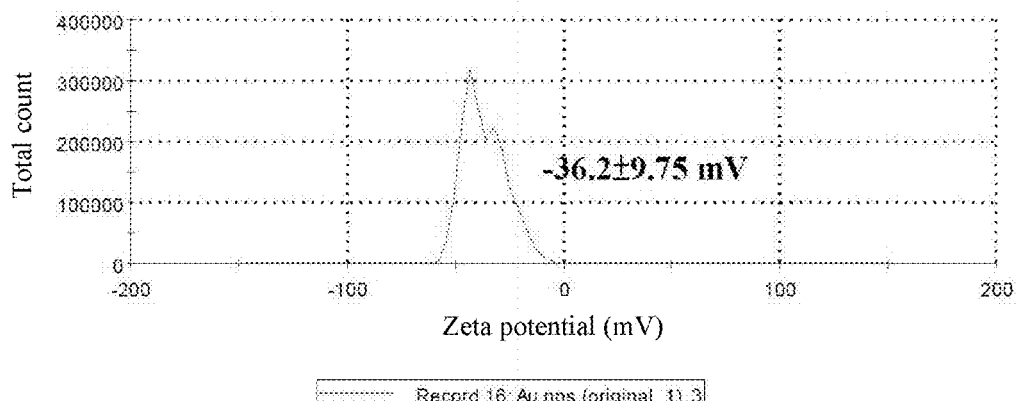
FIG. 12 shows a test result of measuring the zeta potential of BPDA with a dynamic light scatter.

Therefore, in measuring a surface electric valance, first dissolve BPDA in deionized water. Take 1 mL of 1 mg/mL nanoparticle solution and place it in a measuring groove containing an electrode plate, and calculate the electrophoretic mobility with a fixed voltage, so as to obtain a zeta potential (unit being mV). As shown in FIG. 12, the measured result of BPDA is −36.2±9.75 mV.

(III) Preparation Example 2: Synthesis of $^{111}$In-BPDA

Figure 13:
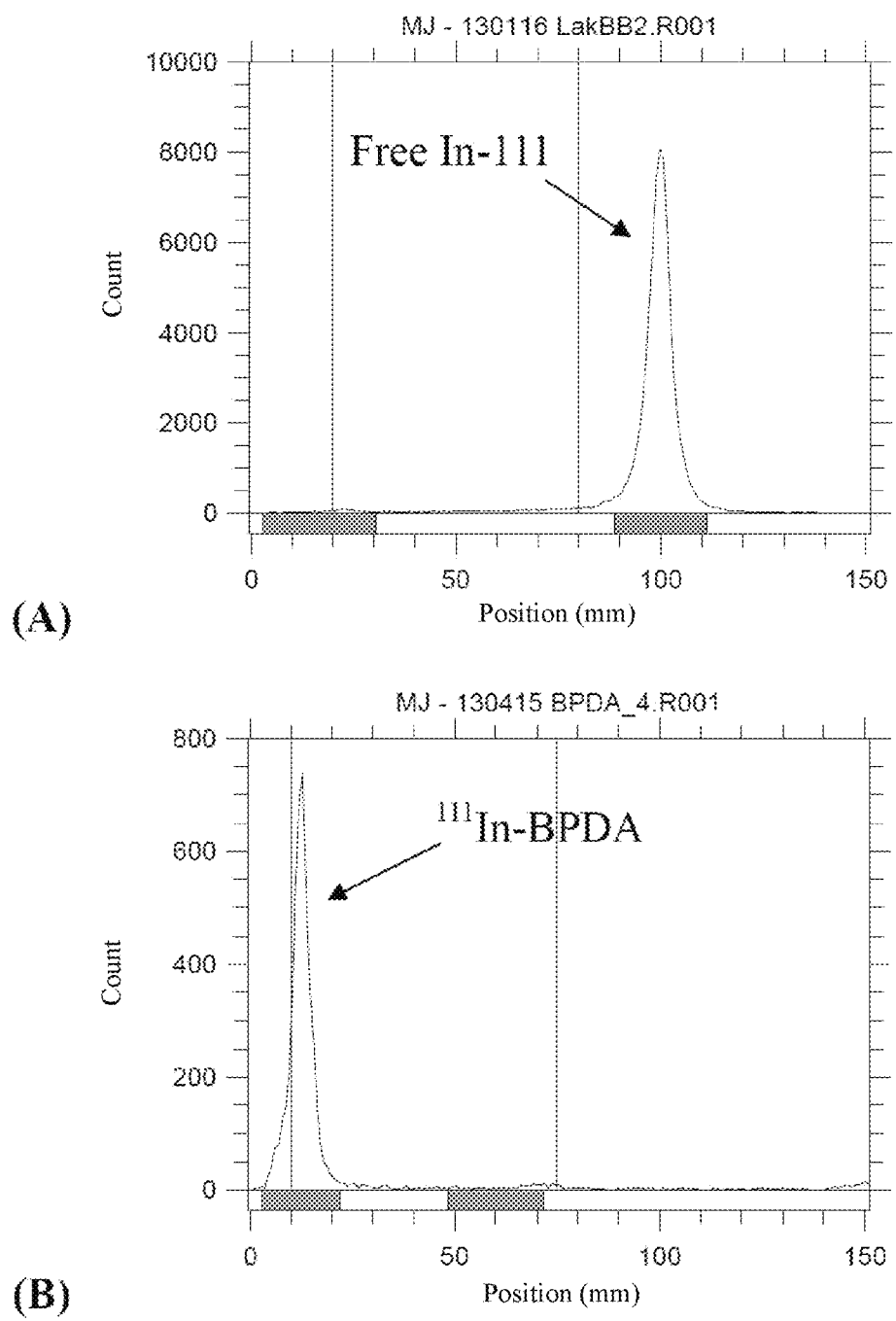
FIG. 13 shows a result of radiochemical synthesis of $^{111}$In-BPDA, in which (A) In-111 isotope is located at the front, and (B)$^{111}$In-BPDA is located at the original point.

Referring to the method disclosed in the prior art (Hao-Wen Kao Y-Y L et al., Evaluation of EGFR-targeted radioimmuno-gold-nanoparticles as a theranostic agent in a tumor animal model. Bioorganic & medicinal chemistry letters 2013, 23:3180-3185.), take 1.6 µg of BPDA (10 µg/25 µL), add a HEPES buffer aqueous solution (0.5 M, pH 6.0) and a demanded radioactive indium-111($^{111}$InCl$_3$) solution in sequence to the total volume of 100 µL, and perform react at 60° C. When the reaction time (30 minutes) is up, perform radio thin-layer chromatography, in which the stationary phase uses ITLC/SG, and the mobile phase is a citrate buffer (0.5 M, pH 6.0 solution). Perform unwrapping and drying. Observe the result of radiochemical purity (R.C.P.) by applying a Radio-TLC reader. As shown in FIG. 13, it can be seen that Rf of the In-111 isotope is at 0.9-1.0, and the Rf of $^{111}$In-BPDA is at 0.0-0.1.

Add 1 mL of water to the $^{111}$In-DTPA-PEG-BBN-AuNPs ($^{111}$In-BPDA) labeled liquid mixture, completely suck and add it to the centrifugation tube eppendorf, perform centrifugation (10 minutes) at 25° C. with a high-speed centrifuge (3,500 rpm), take the supernate, further add 500 µL of water to perform centrifugation, and repeat the step twice. It is found through the test that the supernate has low activity, while in the final product $^{111}$In-BPDA after centrifugation, it is tested that the R.C.P. is greater than 90%, so that the final product can be used to perform in vitro and in vivo tests.

(IV) Test Example 1 of $^{111}$In-BPDA: Drug Stability in Serum FBS and PBS

1. Test Step

Prepare 4 tubes eppendorf. Store 450 µL of fetal bovine serum (FBS) or phosphate-buffered saline (PBS) in each tube. Add 50 µL of $^{111}$In-BPDA solution in each tube (2 tubes before purification and 2 tubes after purification). The activity is about 370 kBq (10 µCi). After even mixing, move them into a 37° C. constant-temperature water bath for culture for 0.5, 1, 2, 4, 17, 24, 42, and 67 hours. After evenly mixing the drug and the FBS or PBS in the tube eppendorf, take a small amount of liquid, measure the R.C.P. of the drug using a radio thin-layer chromatography system (stationary phase: iTLC SG, unwrapped phase: citrate buffer, 0.5 M, pH 6.0), and repeat the measurement three times.

Figure 14:
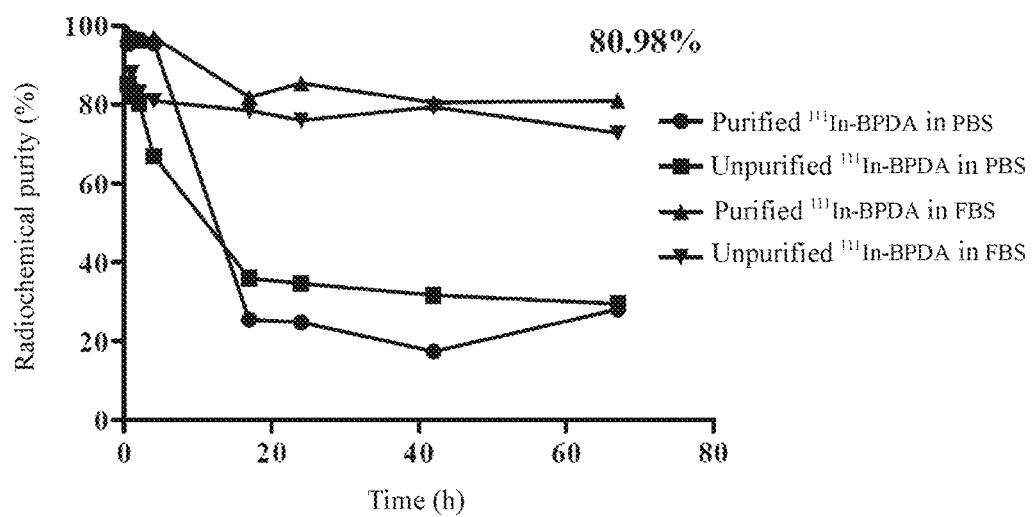
FIG. 14 shows a result of drug stability of liquid mixture after adding $^{111}$In-BPDA before purification and after purification in fetal bovine serum (FBS) or PBS.

Test result: As indicated by the document (Senior J D C, Fisher D, Tilcock C, Gregoriadis G.: Influence of surface hydrophilicity of liposomes on their interaction with plasma protein and clearance from the circulation: studies with poly(ethylene glycol)-coated vesicles. Biochim Biophys Acta 1991, 11:77-82.), because serum contains various proteins such as lysosome or opsonin, both making the drug decompose, a stable drug structure can circulate a longer time in an organism. Therefore, in the test example, $^{111}$In-BPDA before purification and $^{111}$In-BPDA after purification are added in the liquid mixture of fetal bovine serum (FBS) or PBS, the drug stability results are shown in FIG. 14, and the radiochemical purity measured after even mixing both have the trend of gradually decreasing. After 6 hours, in a PBS reaction flask, both $^{111}$In-BPDA before purification and $^{111}$In-BPDA after purification have undesirable results, which might be caused by stability reduction and drug accumulation because the reaction effects of the BPDA and salts.

However, such a phenomenon does not occur in the FBS group. In an FBS reaction flask, it can be seen that $^{111}$In-BPDA after purification has very desirable radiochemical purity (about 80.98%) after 67 hours. Compared with the PBS, the FBS is closer to the in vivo environment of an animal where the drug is injected. This result shows that the radioactive targeted gold nanoparticles $^{111}$In-BPDA should have desirable stability within 67 hours in an animal body.

(V) Test Example 2 of $^{111}$In-BPDA: In Vitro Test

1. Cell Culture

The entire cell culture is processed in a sterile laminar flow cabinet. A human prostate cancer cell strain PC-3 (human prostate cancer) is cultured in a constant-temperature chemostat of 37° C. and filled with 5% CO2 with an RPMI 1640 culture medium containing 10% of fetal bovine serum (FBS) and 1% of PS. The human breast cancer cell strain MB231 is cultured with a DMEM culture medium with 10% of FBS and 1% of PS.

2. Cell Uptake Test

Amplify PC-3 and MB231 cells first before the test, and plant the two types of cells in different 96 well plates, respectively. In each test, the well plate of the same type of cells is grouped into a radiation drug uptake group (used for observing uptake of the drug) and an MTT group (for the MTT test (the method is referred to the document: Wan F, You J, Sun Y, Zhang X G, Cui F D, Du Y Z, Yuan H, Hu F Q: Studies on PEG-modified SLNs loading vinorelbine bitartrate (I): preparation and evaluation in vitro. Int J Pharm 2008, 359:104-110, to evaluate the number of cells). Before the MTT test, dilute a 10×MTT solution (50 mg/mL dissolved in water three times) with a free medium into a 1×MTT solution for use. The manner of the test is as follows:

(1) Plant $2 \times 10^4$ PC-3 or MB231 cells in each well. After 24 hours of culture, first remove the culture medium. Further add different drugs to observe the accumulation conditions. Add $^{111}$In-BPDA (0.1 µCi/200 µL free medium) of the same concentration in each well, and perform culture for 0.5, 1, 2, 4, and 24 hours at 37° C. (two types of cells, each drug, each time, repeating at least three times).

(2) At the test time point, suck the cell culture media in each well in the radiation drug uptake group, and clean the cell gently with 200 µL of PBS (pH 7.3), and repeat the process three times. Place the sucked liquid in a counter tube, and measure the activity using a gamma counter.

(3) Next, add 50 µL of trypsin in each well in the radiation drug uptake group, further suck the cellular fluid after 3 hours, clean the cells with 200 µL of PBS, repeat the process three times, place the sucked liquid in a counter tube, and measure the activity using a gamma counter. The activity of the cells is normalized into the uptake activity of $1 \times 10^7$ cells, and is divided by the activity of the culture medium to obtain the C/M ratio.

(4) In the MTT group, when the culture is ended, suck the cell culture media in the wells, and clean the cells three times gently using 200 µL of PBS. Next, add 100 µL of 1×MTT solution diluted in advance (the concentration being 5 mg/mL) to perform an MTT test. After 3 hours of culture, remove the MTT solution from the wells. Next, add 200 µL of DMSO to dissolve the dark purple precipitate MTT formazan. Shake several times for thorough dissolution. Finally, place the 96 well plate in an ELISA reader to measure the light absorption value (OD value) (the wavelength of reading is set to be 570 nm), and convert the value into the number of cells (calculated through the standard curve having an OD value corresponding to each number of cells, and the standard curve test is performed in advance).

Figure 15:
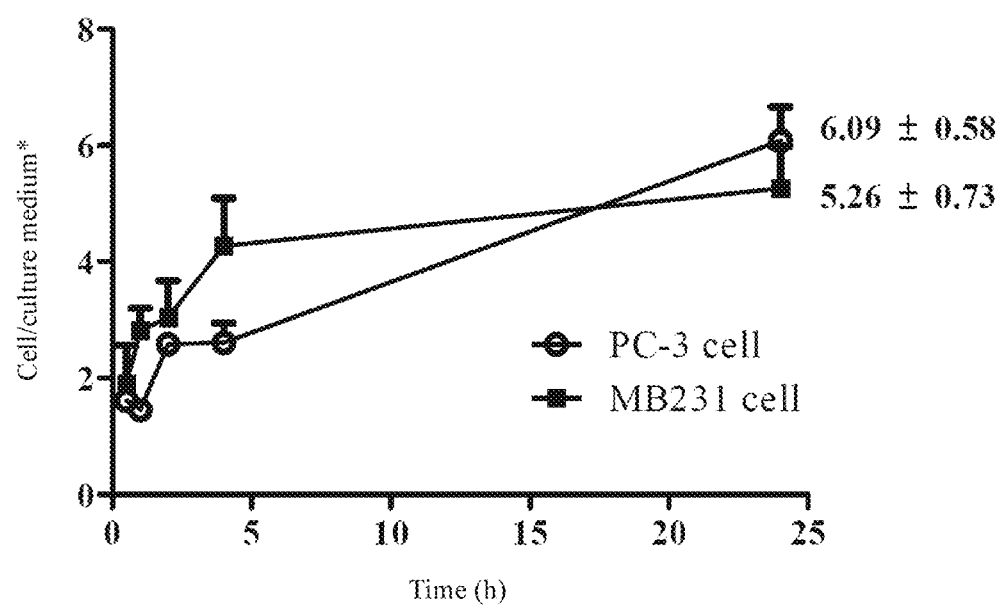
FIG. 15 shows a cell uptake result after adding $^{111}$In-BPDA in PC-3 and MB231 cells for 0.5, 1, 2, 4, and 24 hours, and cell-to-medium (C/M) ratios of two cells after 24 hours are calculated (n=3)

Test result: 0.5, 1, 2, 4, and 24 hours after $^{111}$In-BPDA is added in the cells, the result of cell-to-medium ratio (C/M ratio) at each time point can be obtained. As shown in FIG. 15, within 24 hours, the uptake of $^{111}$In-BPDA by the PC-3 and MB231 cells gradually rises, and reaches the maximum after 24 hours. The C/M ratios of PC-3 and MB231 after 24 hours are 6.09±0.58 and 5.26±0.73, respectively.

Through the result of the cell uptake test, it can be predicted that after $^{111}$In-BPDA is injected in a nude mouse carrying PC-3 tumor, the accumulation at the tumor gradually rises after 1 hour, reaches the maximum after 24 hours, and might stay in the tumor for a period of time.

(VI) Test Example 3 of $^{111}$in-BPDA: In Vivo Test

1. Tumor Induction

First, complete the preparation of instruments required by the test, a PC-3 tumor cell (the concentration being 2×10$^6$ cells dissolved in 100 μL of PBS) suspension, and anesthetics for anesthetizing animals, and ensure the sterilization of the instruments. After anesthetizing a nude mouse, extract the tumor cell suspension with a syringe to perform hypodermic injection. After a proper period of time (about two weeks later), the tumor is successfully induced to a proper size (100 mm$^3$) to perform the animal test.

2. Biodistribution Test of Tumor-Carrying Mouse

Perform the biodistribution test using mice (6) carrying PC-3 tumor, and select 4 and 24 hours as the test time points. Group the mice into 2 groups, and each group has 3. 1.11 MBq (30 μCi in 100 μL) of $^{111}$In-BPDA is injected to each mouse through the tail vein, respectively. 4 and 24 hours after injection, sacrifice one group of mice, respectively. Pick organ samples rapidly, which comprise organs such as blood, lung, heart, liver, small intestine, large intestine, kidney, spleen, urinary bladder, urine, and muscle and the tumor, and weight the weight of the organs, respectively. Finally, measure the radioactivity of each organ by applying a gamma counter, and divide the activity and the weight, and perform normalization to obtain % ID/g (% injection dose per gram of organ) of each organ. Divide the tumor and the % ID/g of muscle, the tumor-muscle ratio (T/M ratio) can be calculated.

Test result: 4 and 24 hours after $^{111}$In-BPDA is injected to the mice carrying PC-3 tumor through the vein, sacrifice one group of mice to perform the biodistribution test, respectively, and calculate % ID/g and standard deviation of each organ, and the result is shown in Table 3. After 4 hours, organs such as blood, liver, spleen, urinary bladder, and urine have high-activity accumulation. It is estimated that nanoparticles are engulfed by the reticuloendothelial system (for example, liver and spleen) and then eliminated by the circulatory system, which therefore results in distinct radioactive accumulation. After 24 hours, it can be found that the activity in blood and urine decreases, but liver and spleen still have the high accumulation behavior. In the brain, muscle, and testicle, a quite low accumulation behavior at each time point can be seen. % ID/g±SD in the PC-3 tumor gradually increases to 1.18±0.66 from 4 hours to 24 hours. By dividing the activity of the tumor and the activity of the muscle, it can be found that the T/M ratios after 4 and 24 hours are 3.88±2.01 and 8.00±2.99, respectively, showing that the radioactive targeted gold nanoparticles $^{111}$In-BPDA has a high accumulation behavior in the tumor, and the result is especially distinct after 24 hours.

TABLE 3

Biodistribution test result (n = 3) of 4 and 24 hours after injecting $^{111}$In-BPDA to a mouse carrying PC-3 tumor through the tail vein, values being represented by % ID/g.

| Time (h) | 4 | 24 |
|---|---|---|
| Brain | 0.06 ± 0.01 | 0.04 ± 0.02 |
| Muscle | 0.21 ± 0.06 | 0.15 ± 0.07 |
| Bone | 0.87 ± 0.20 | 0.96 ± 0.59 |
| Stomach | 0.46 ± 0.05 | 0.49 ± 0.15 |
| Spleen | 8.43 ± 0.73 | 8.84 ± 2.66 |
| Pancreas | 0.39 ± 0.18 | 0.60 ± 0.26 |
| Liver | 58.01 ± 0.89 | 41.63 ± 4.27 |
| Small intestine | 1.09 ± 1.19 | 0.76 ± 0.38 |
| Large intestine | 0.66 ± 0.31 | 0.66 ± 0.15 |
| Blood | 4.77 ± 6.34 | 0.45 ± 0.20 |
| Lung | 1.53 ± 0.50 | 1.31 ± 0.68 |
| Heart | 0.46 ± 0.07 | 0.34 ± 0.16 |
| Kidney | 7.56 ± 3.08 | 4.55 ± 1.24 |
| Tumor | 0.89 ± 0.70 | 1.18 ± 0.66 |
| Gallbladder | 3.30 ± 5.23 | 0.50 ± 0.13 |
| Urine | 113.34 ± 183.80 | 4.62 ± 0.41 |
| Excrement | 0.53 ± 0.34 | 1.25 ± 0.70 |
| Testicle | 0.35 ± 0.06 | 0.34 ± 0.14 |
| T/M ratio | 3.88 ± 2.01 | 8.00 ± 2.99 |

Data is expressed by % ID/gm ± SD

3. Single-Photon Scintillation Imaging/Computed Tomography Test on Tumor-Carrying Mouse After the mice carrying PC-3 tumor are anesthetized, inject 11.1 MBq (300 μCi in 100 μL) of $^{111}$In-BPDA through the tail vein, respectively. Select 1, 4, 24 and 48 hours to apply high-resolution small-animal single-photon scintillation imaging/computed tomography (SPECT/CT) to perform generalized radioactive medicine distribution scanning on the mice carrying PC-3 tumor (it is set that each group has 3 mice), so as to observe the maximum accumulation time and the retention behavior of the drug at the tumor. After recombination and fusion of the CT and SPECT images, select a region of interest (ROI) by applying Pmod software, so as to obtain a T/M ratio.

Figure 16:
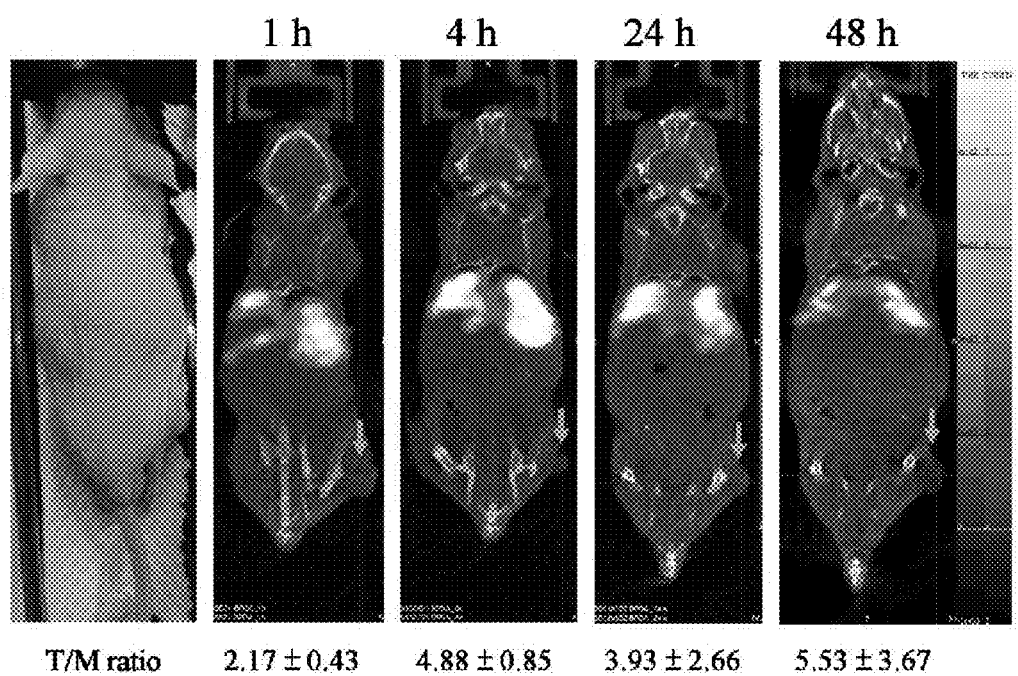
FIG. 16 shows a result of SPECT/CT coronal view images and T/M ratios after injecting $^{111}$In-BPDA in a mouse carrying PC-3 tumor for 1, 4, 24, and 48 hours, in which the arrow indicates the position of the tumor (n=3).

Test result: After the mice carrying PC-3 tumor are anesthetized, inject 11.1 MBq (300 μCi in 100 μL) of $^{111}$In-BPDA through the tail vein, respectively. The result of performing generalized radioactive medicine distribution scanning on the test animals by applying high-resolution small-animal single-photon scintillation imaging/computed tomography (SPECT/CT) 1, 4, 24, and 48 hours after injection is shown in FIG. 16.

The leftmost is the photo of the mouse, and SPECT/CT images are images of the coronal view at the time points, in which green arrows indicate the position of the tumor. It is seen in the images that the major accumulation organ is liver, and the accumulation of tumor is indistinct. However, after selecting an ROI by applying Pmod software, the T/M ratio can be obtained. The result shows that: from 1 hour to 48 hours, the T/M ratio gradually rises, the T/M ratio is 4.88±0.85 at 4 hours, 3.93±2.66 at 24 hours, and after 48 hours, reaches the maximum 5.53±3.67 for the accumulation in the tumor. Such a result is very consistent with the result of the biodistribution test, showing that the radiolabeled active targeting pharmaceutical composition $^{111}$In-BPDA accumulates at the tumor within 24 hours, and keeps accumulating at the tumor within 48 hours, which shows the desirable targeting characteristic thereof.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A radiolabeled active targeting pharmaceutical composition, comprising:
   a bioconjugate, comprising a peptide, a metal nanoparticle, and an intercalating agent, wherein the peptide is a Bombesin (BBN) peptide combined with maleimidolipoamide, the intercalating agent is diethylene triamine pentaacetic acid (DTPA), and the metal nanoparticle is Au nanoparticle; and
   a radionuclide, selected from the group consisting of: indium, iodine, lutetium, rhenium, gallium, and yttrium.

2. The pharmaceutical composition according to claim 1, wherein the metal nanoparticle further has a thiol group through surface modification.

* * * * *